US010327990B2

(12) United States Patent
Egeland et al.

(10) Patent No.: US 10,327,990 B2
(45) Date of Patent: Jun. 25, 2019

(54) CONTAINER FOR MIXING AND DISPENSING FLUID MEDICATION COMPONENTS

(71) Applicant: 3M INNOVATIVE PROPERTIES COMPANY, Saint Paul, MN (US)

(72) Inventors: Marc A. Egeland, Saint Paul, MN (US); Chin-Yee Ng, Oakdale, MN (US); Jo A. Etter, Roseville, MN (US); Ravi Kolakaluri, Roseville, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 35 days.

(21) Appl. No.: 15/537,040

(22) PCT Filed: Dec. 22, 2015

(86) PCT No.: PCT/US2015/067379
§ 371 (c)(1),
(2) Date: Jun. 16, 2017

(87) PCT Pub. No.: WO2016/109339
PCT Pub. Date: Jul. 7, 2016

(65) Prior Publication Data
US 2018/0049948 A1 Feb. 22, 2018

Related U.S. Application Data

(60) Provisional application No. 62/098,079, filed on Dec. 30, 2014.

(51) Int. Cl.
*A61J 1/20* (2006.01)
*A61M 5/24* (2006.01)
(Continued)

(52) U.S. Cl.
CPC .......... *A61J 1/2093* (2013.01); *A61M 5/2448* (2013.01); *A61M 5/284* (2013.01);
(Continued)

(58) Field of Classification Search
CPC ............ A61M 5/19; A61M 2005/1787; A61M 5/2448; A61M 5/3294; A61M 5/284;
(Continued)

(56) References Cited

U.S. PATENT DOCUMENTS

| 4,254,768 A | 3/1981 | Ty |
| 4,874,381 A | 10/1989 | Vetter |

(Continued)

FOREIGN PATENT DOCUMENTS

| CA | 2016870 | 11/1991 |
| EP | 0172990 | 3/1986 |

(Continued)

OTHER PUBLICATIONS

International Search Report for PCT International Application No. PCT/US2015/067379, dated Apr. 1, 2016, 7pgs.

*Primary Examiner* — Manuel A Mendez
(74) *Attorney, Agent, or Firm* — Eric E. Silverman

(57) ABSTRACT

A container for storing and mixing two components is provided. The container includes a body, a first plug, and a second plug. The body has a first end, a second end, and a bypass with a length L disposed between the first and second ends. The first and second plugs are slidably disposed in the body and define a first compartment. A second compartment is in the body between the second plug and the second end. The second plug has a first edge, a second edge, and a primary conduit extending therein, a plurality of secondary conduits extending from the primary conduit through the second plug. The primary conduit has a first opening. A distance D extends longitudinally from the first edge to the (Continued)

second edge and a distance E extends longitudinally from the first edge to the first opening. D≥L and E<L.

20 Claims, 9 Drawing Sheets

(51) Int. Cl.
*A61M 5/28* (2006.01)
*A61M 5/31* (2006.01)
*A61M 5/315* (2006.01)

(52) U.S. Cl.
CPC .......... *A61M 5/315* (2013.01); *A61M 5/3129* (2013.01); *A61M 5/31596* (2013.01); *A61M 5/3137* (2013.01); *A61M 5/31511* (2013.01); *A61M 5/31513* (2013.01); *A61M 2005/31523* (2013.01)

(58) Field of Classification Search
CPC ................ A61M 5/3129; A61M 5/315; A61M 5/31596; A61J 1/2093
USPC .................................................. 604/191, 218
See application file for complete search history.

(56) References Cited

U.S. PATENT DOCUMENTS

| | | |
|---|---|---|
| 5,080,649 A | 1/1992 | Vetter |
| 5,320,603 A | 6/1994 | Vetter |
| 5,788,670 A | 8/1998 | Reinhard |
| 5,791,466 A | 8/1998 | Tsals |
| 5,830,193 A | 11/1998 | Higashikawa |
| 5,865,798 A | 2/1999 | Grimard |
| 7,981,076 B2 | 7/2011 | Sullivan |
| 8,002,734 B2 | 8/2011 | Bassarab |
| 2003/0036724 A1 | 2/2003 | Vetter |
| 2004/0228769 A1 | 11/2004 | Taylor |
| 2007/0060875 A1 | 3/2007 | Bassarab |
| 2007/0129673 A1 | 6/2007 | Bassarab |
| 2008/0045889 A1 | 2/2008 | Gerondale |

FOREIGN PATENT DOCUMENTS

| | | |
|---|---|---|
| EP | 0295337 | 12/1988 |
| EP | 0440846 | 8/1991 |
| EP | 0599649 | 6/1994 |
| EP | 0664136 | 7/1995 |
| EP | 0718002 | 6/1996 |
| EP | 0815886 | 1/1998 |
| EP | 1287841 | 3/2003 |
| EP | 1728528 | 12/2006 |
| EP | 2641628 | 9/2013 |
| JP | 2005-185747 | 7/2005 |
| WO | WO 2002-089960 | 11/2002 |
| WO | WO 2007-020239 | 2/2007 |
| WO | WO 2008-150208 | 12/2008 |
| WO | WO 2013-163598 | 10/2013 |
| WO | WO 2016-109336 | 7/2014 |
| WO | WO 2016-109342 | 7/2014 |

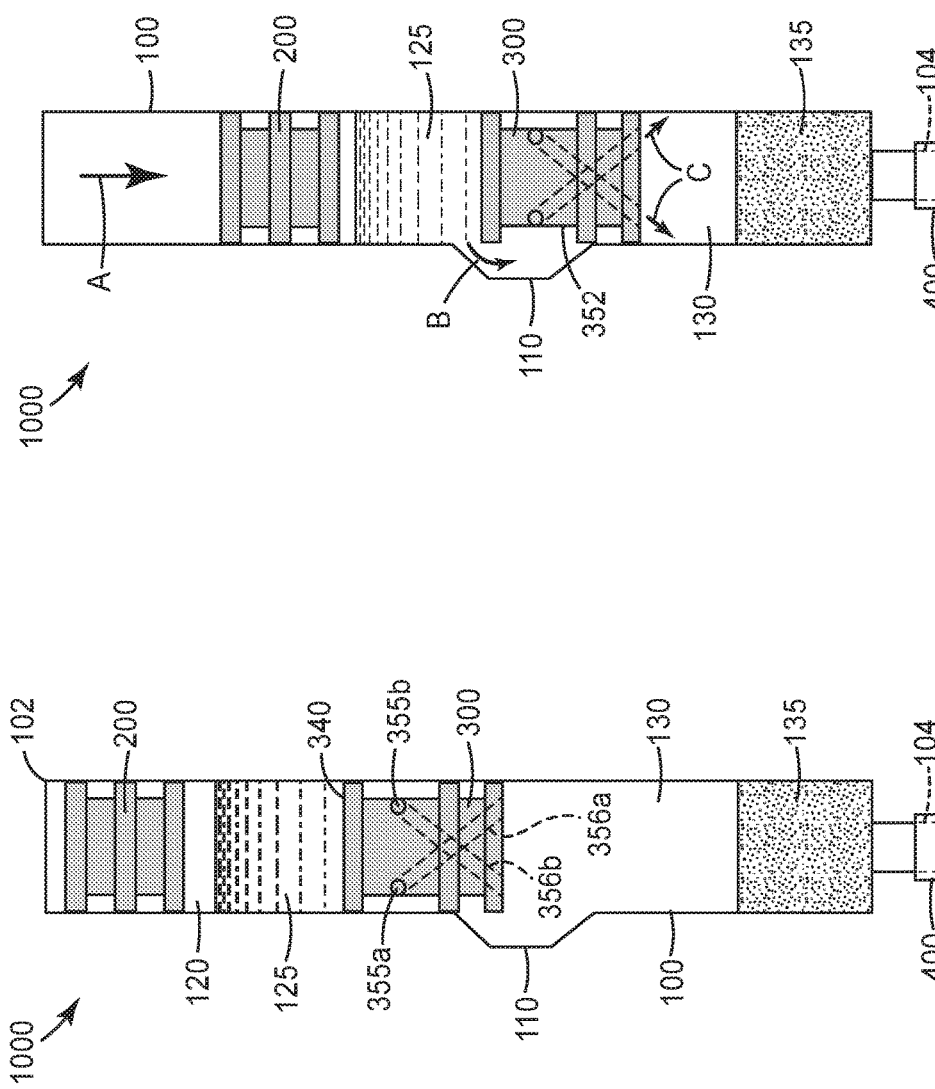

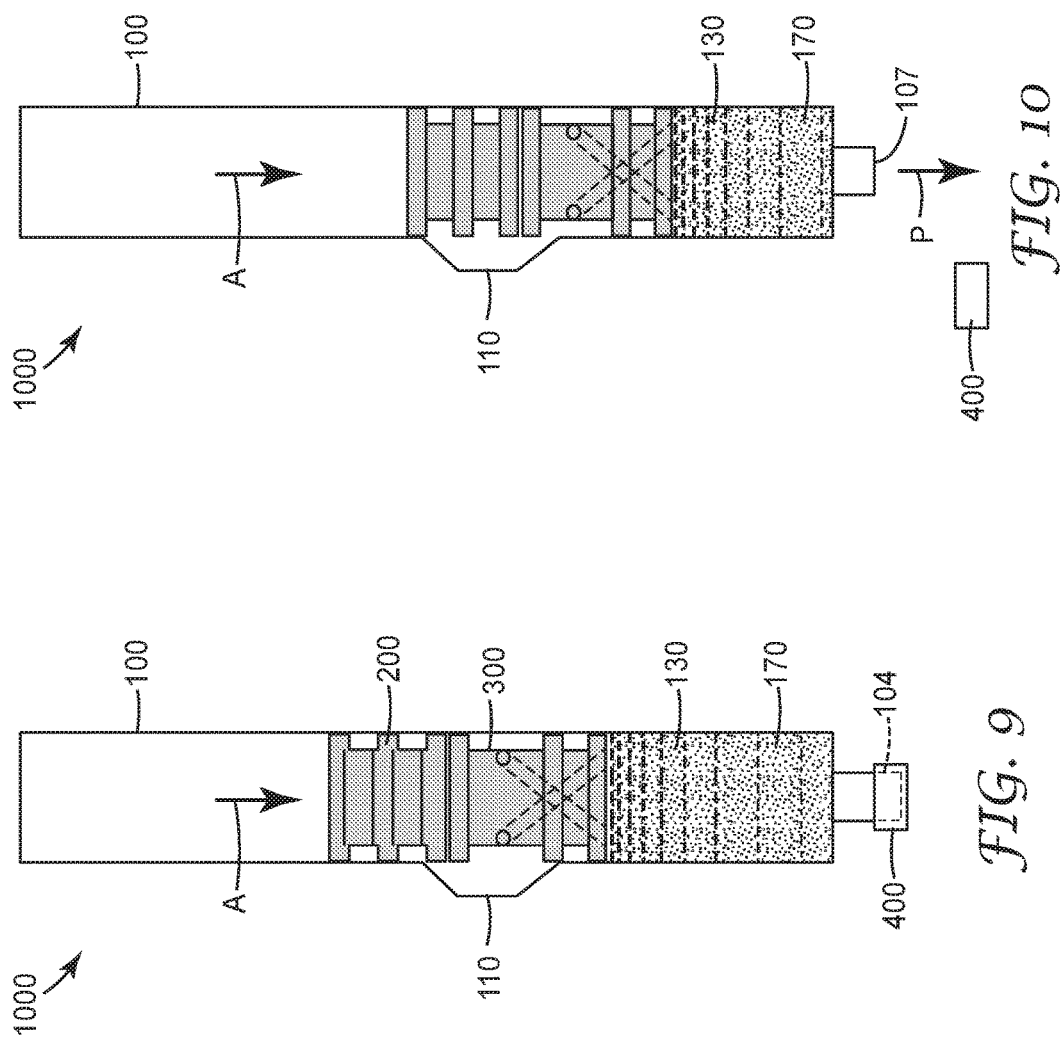

CONTAINER FOR MIXING AND DISPENSING FLUID MEDICATION COMPONENTS

CROSS REFERENCE TO RELATED APPLICATIONS

This application is a national stage filing under 35 U.S.C. 371 of PCT/US2015/067379, filed Dec. 22, 2015, which claims the benefit of U.S. Provisional Application No. 62/098,079, filed Dec. 30, 2014, the disclosures of which are incorporated by reference in their entirety herein.

BACKGROUND

A standard hypodermic syringe comprises a cylindrically tubular body having a front end closed by a plug formed with a central passage extending along the axis of the body and a rear end provided with a piston longitudinally axially displaceable in the body. A quantity of liquid to be injected is held in the body between the piston and the plug and a needle is fitted to the passage at its front end so that forward displacement of the piston by a plunger forces the liquid out of the body through the needle.

A syringe for one-time use is frequently supplied already containing a lyophilized medicament, to which some solvent, for instance sterile water, is added to make the dried medicament injectable. To prepare the syringe for use a needle is mounted on the front end of the body and the liquid is drawn into it.

It is also possible as described in U.S. Pat. No. 4,874,381 for there to be two pistons, namely a front piston that subdivides the interior of the body into a rear compartment holding the dry medicament and a front compartment holding a solvent, typically water, for it. In this case the body is formed with a bypass that permits mixing of the medicament and the liquid on axial displacement of the pistons. A rear piston is advanced to eject the contents.

In both systems the syringe is initially prepared by filling into the body a quantity of the dissolved medicament and then lyophilizing it and driving off the vaporized solvent, which escapes through the open front end of the cylinder. While maintaining sterility the front end is plugged, and the thus prepared syringe is then fitted with the necessary tip cap or the like, and is bagged.

Such an arrangement is not readily susceptible to mass production, as it is necessary to hold down costs of this throwaway item. In fact production is fairly difficult in view of the problems associated with plugging the cylinder end while maintaining the syringe and its environs sterile.

SUMMARY

The present disclosure generally relates to a container for isolating (for storage) two components and, subsequently, rapidly and easily bringing the two components together in the container. Optionally, the container can also be used to distribute the mixture of the components. Although particularly useful for storing and reconstituting dehydrated pharmaceutical preparations, a person having ordinary skill in the art will recognize the container and method is useful for storing and preparing a variety of reconstitutable compositions. The turbulence generated by a second plug disposed in the inventive container facilitates rapid dissolution and/or dispersion of a solid component in a liquid reconstitution medium.

In one aspect, the present disclosure provides a container. The container can comprise a body, a first plug and a second plug. The body has a longitudinal axis, a first end with a first aperture, a second end including a second aperture opposite the first end, and a bypass having a length L disposed between the first and second ends. The first plug can be slidably disposed in the body proximate the first end. The second plug can be slidably disposed in the body between the first plug and the second end. The first and second plugs can define opposite ends of a first compartment disposed in the body between them. A second compartment can be disposed in the body between the second plug and the second end. The second plug can include a top surface facing the first plug; a bottom surface facing the second end; a side wall extending between the top surface and the bottom surface, the side wall comprising a circumferential first seal having a first edge proximate the top surface and a circumferential second seal having a second edge proximate the bottom surface; a primary conduit extending into the second plug from a first opening in the side wall; and a plurality of secondary conduits, each secondary conduit extending from the primary conduit to separate second openings in the bottom surface. The first opening is disposed between the circumferential first seal and the circumferential second seal. At least one of the secondary conduits can direct liquid flow out of the second opening along a line that is not parallel to the longitudinal axis. A distance D extends longitudinally from the first edge to the second edge of the second plug, a distance E extends longitudinally from the first edge to the first opening and D≥L and E<L.

In another aspect, the present disclosure provides a method of mixing first and second components of a composition. The method can comprise providing a container according to any one of the above embodiments, wherein the container has the first component disposed in the first compartment and the second component disposed in the second compartment. The method further can comprise bringing the first component into contact with the second component. The first component can comprise a fluid. The second component can comprise a fluid or a solid. Bringing the first component into contact with the second component can comprise urging the first plug toward the second end until the first opening is in fluid communication with the bypass, the first compartment, and the second compartment. Urging the first plug toward the second end can comprise urging at least a portion of the first component from the first compartment into the second compartment.

In yet another aspect, the present disclosure provides a method of mixing first and second components of a composition and distributing the composition. The method can comprise providing a container according to any one of the above embodiments, wherein the container has the first component disposed in the first compartment and the second component disposed in the second compartment. The method further can comprise bringing the first component into contact with the second component. The first component can comprise a fluid. The second component can comprise a fluid or a solid. Bringing the first component into contact with the second component can comprise urging the first plug toward the second end until the first opening is in fluid communication with the bypass, the first compartment, and the second compartment. Urging the first plug toward the second end can comprise transferring a predetermined volume of the first component from the first compartment into the second compartment to form the composition. After the predetermined volume of the first component is transferred into the second compartment, urging the first plug toward the second end further comprises urging the second plug toward the second end. Urging the second plug toward the second end comprises distributing at least a portion of the composition out of the body via the second aperture. In any of the above embodiments, converting the second end of the container from a closed state to an open state comprises converting a fluid-tight seal from a closed state to an open state. In any of the above embodiments, the method further can comprise coupling the second end to an infusion device.

The terms "comprises" and variations thereof do not have a limiting meaning where these terms appear in the description and claims.

As used herein, "a," "an," "the," "at least one," and "one or more" are used interchangeably. Thus, for example, a channel can be interpreted to mean "one or more" channels.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF DRAWINGS

FIG. 7 is a schematic side view, partially in section, of one embodiment of a container according to the present disclosure, wherein the container holds a first component in the first compartment and a second component in the second compartment, and wherein the second plug is disposed in a first operational position with respect to the bypass.

FIG. 8 is a schematic side view, partially in section, of the container of FIG. 7, wherein the second plug is disposed in a second operational position with respect to the bypass.

FIG. 9 is a schematic side view, partially in section, of the container of FIG. 8, wherein the entirety of the first and second components are blended in the second compartment and the first and second plugs are positioned to expel the blended components out of the container.

FIG. 10 is a schematic side view of the container of FIG. 9 showing the expulsion of its contents after removal of the seal.

DETAILED DESCRIPTION

Figures 1, 2:
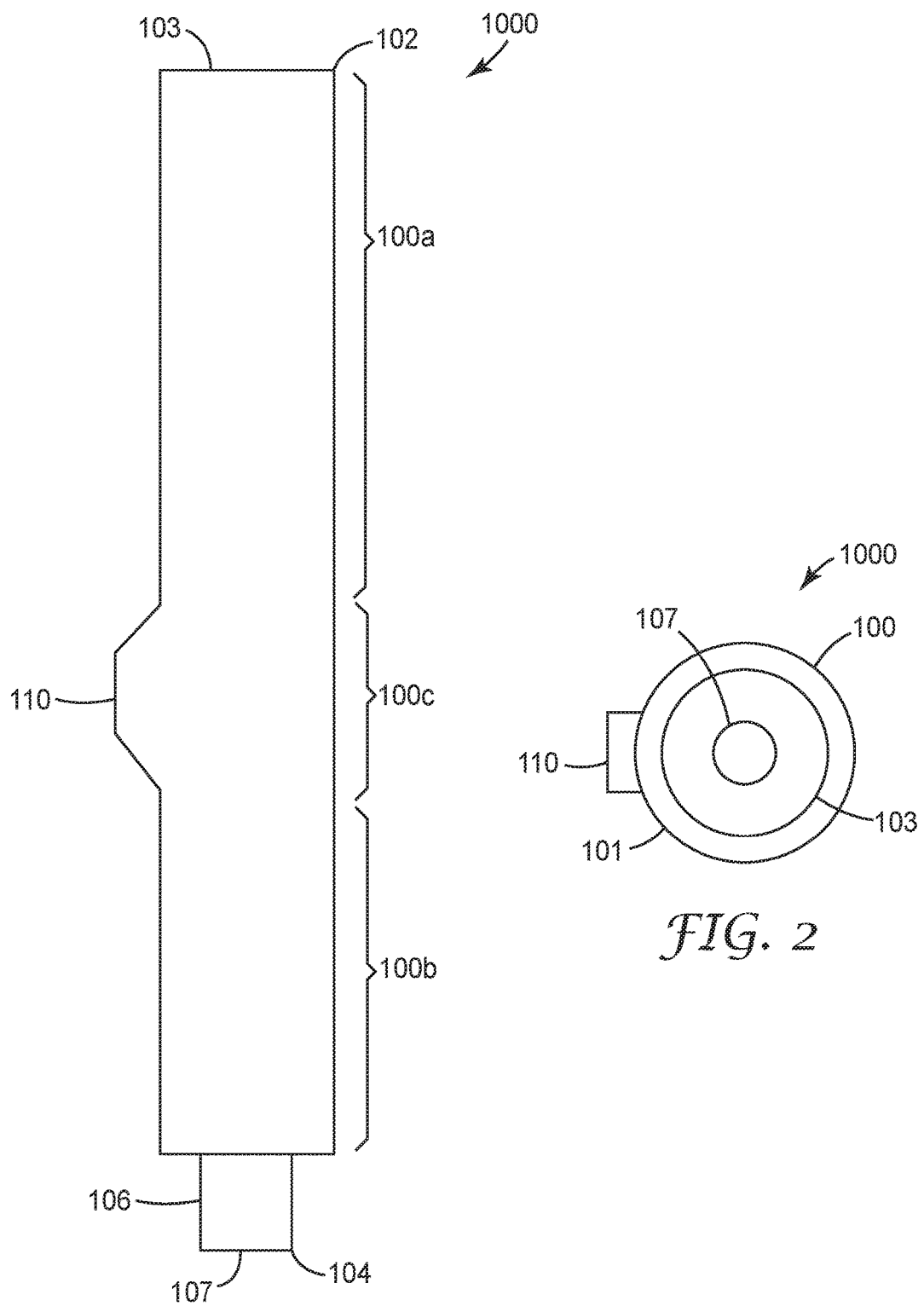
FIG. 1 is a schematic side view, partially in section, of one embodiment of a container according to the present disclosure.
FIG. 2 is a top view of the body of the container of FIG. 1

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the device, to indicate or imply necessary or required orientations of the device, or to specify how the invention described herein will be used, mounted, displayed, or positioned in use.

The present disclosure generally relates to a container for initially holding in separate compartments two components to be mixed, for subsequently bringing together the two components and for distributing the resulting combination of the two components. In addition, the present disclosure relates to methods of preparing the container with the isolated components therein and to methods of using the container to combine and, optionally, distribute the resulting combined components. Advantageously, the container of the present disclosure provides improved mixing of the components during use.

The present disclosure provides a container. In any embodiment, the container comprises:
  a body having a longitudinal axis, a first end with a first aperture, a second end including a second aperture opposite the first end, and a bypass disposed between the first and second ends;
    wherein the bypass has a length L;
  a first plug slidably disposed in the body proximate the first end;

a second plug slidably disposed in the body between the first plug and the second end;
   wherein the first and second plugs define a first compartment disposed in the body between them;
   wherein a second compartment is disposed in the body between the second plug and the second end;
   wherein the second plug includes:
      a top surface facing the first plug;
      a bottom surface facing the second end;
      a side wall extending between the top surface and the bottom surface, the side wall comprising a circumferential first seal having a first edge proximate the top surface and a circumferential second seal having a second edge proximate the bottom surface;
      a primary conduit extending into the second plug from a first opening in the side wall; and
      a plurality of secondary conduits, each secondary conduit extending from the primary conduit to separate second openings in the bottom surface;
      wherein the first opening is disposed between the circumferential first seal and the circumferential second seal;
      wherein at least one of the secondary conduits directs liquid flow out of its second opening along a line that is not parallel to the longitudinal axis;
      wherein a distance D extends longitudinally from the first edge to the second edge;
      wherein a distance E extends longitudinally from the first edge to the first opening;
         wherein D≥L and E<L.

A container according to the present disclosure has a body (e.g., a tubular body) having an interior volume and extending along and centered on an axis. The body has at an axial first end with a first aperture that provides access to at least a portion of the inner volume of the body. The body has at an axial second end a second opening opposite the first aperture.

In any embodiment, the second end further comprises a coupling structure. The coupling structure may be adapted to couple the container to a needle or a microneedle device, for example. Non-limiting examples of suitable coupling structures include Luer fittings (e.g., Luer-slip and Luer-lock type fittings) that are well known in the art. In any embodiment, the coupling structure can couple the container to an infusion device. Nonlimiting examples of infusion devices include a catheter, a cannula, a needle, or a microneedle device.

There are pharmaceutical compositions which, in a liquid state, very rapidly lose their efficacy. To enable these compositions to be used in spite of their short shelf life, special devices and methods of lyophilization have been developed. Thus, pharmaceutical preparations which cannot be used in solution over long periods may be made durable by lyophilization, for example, and possibly stored away from light. The dry substance is only dissolved again, i.e., reconstituted, immediately before use. For this purpose two-component systems have become known for re-dissolving the lyophilizate immediately before use.

Other solutions have been sought for carrying out lyophilization of the solid substance present in the solution using double compartment systems of this kind, to produce a product that can be re-dissolved subsequently or after corresponding storage before use, i.e., to allow the two component systems to be mixed together, while maintaining the sterility of the two components. The lyophilization of solutions in a syringe is only possible under special conditions, one problem being that during the lyophilization only a very small cross sectional area is available for the exchange of gases. The prior art contains numerous proposals for solving these problems including, for example, those described in U.S. Pat. Nos. 5,788,670; 4,254,768; 8,002,734; and EP Patent Publication Nos. 0 718 002 A2 and 0 295 337 B1; which are all incorporated herein by reference in their entireties. Each of the recited proposals has inherent disadvantages that make them less useful than the container of the present disclosure.

The disadvantages show that there is still a need for an easy to operate device for reliably storing and mixing two-component systems and further to dispense the mixture (or suspension) of the two components. In any embodiment, one component (e.g., a second component as described herein) of the two-component system is a gas, a liquid, a gel, a substantially dry solid (e.g., a lyophilizate), or a paste, and the other component (e.g., a first component as described herein) of the two-component system is a dissolving/dispersing medium (e.g., a gas, a liquid, a gel) therefor. In particular it should be possible to carry out lyophilization directly in the container, while avoiding the disadvantages of the prior art. Contamination from outside should be ruled out as far as possible. In particular, subsequent mixing should take place without removing the components from the sterile inner part of the device and without any external intervention in the system thereby compromising the sterile condition. The device should also be easy to store. Furthermore, a method of easily filling a device of this kind should be provided. The device and the method should be usable on an industrial scale.

The objective described above is achieved by means of the features of any embodiment of the containers of the present disclosure. These embodiments provide a double compartment container for separately holding and combining a solid lyophilizate and a liquid reconstitution medium therefor.

In the filled state the container also serves to store or preserve the lyophilizate component and a reconstitution medium component therefor in separate compartments. The two components can be mixed together immediately before use without the need to open the container. By combining the two components it is possible for example to prepare an injectable solution either in dissolved or dispersed form. In any embodiment, the reconstitution medium may comprise water but also may be some other solvent or mixture of solvents.

The body (e.g., cylindrical body) according to the present disclosure is an essentially elongate hollow body with two open ends which has preferably been formed integrally, i.e., made in one piece. The "cylindrical" body need not necessarily be cylindrical in shape, although this is the most common shape. Any other geometric shape for an elongate hollow body is possible, such as angular or oval, for example, in which case the closures and separating stopper and the like should be matched to the chosen shape. The material of which the body consists or which it contains is not particularly restricted according to the invention. The container may be selected for example from plastics or glass. In any embodiment, glass may be preferred on account of its transparency and its compatibility with numerous medical formulations. The body therefore preferably consists of glass or contains glass, as this produces the least effect on the components contained therein and the body is preferably transparent. For particular requirements, however, other materials may be suitable, such as special plastics (e.g., cyclic olefin copolymers) or the like. Medical safety is particularly important, as it is desirable that there be as little interaction as possible with the medium contained therein.

The double compartment container further comprises two plugs, a second plug that is provided at a second end (e.g., in which a solid component to be mixed is disposed) and a first plug that is provided at a first end (e.g., in which a liquid component to be mixed with the solid component is disposed) of the container. The plugs are not restricted further provided that the first plug enables pressure to be applied to the liquid for mixing the two components, so that the second plug moves out of its position and can be pushed into the bypass.

The first plug is preferably a stopper which provides a suitable seal, is inert relative to the medium to be added, and satisfies the sterility conditions. The first plug should be of such a size or shape that any openings proximate the first end of the body are sealed off by it in the second position of the stopper.

The second plug arranged in the cylindrical body defines the size/volume/dimensions of the two compartments and functions as a selective barrier to regulate passage into the second compartment of any contents (e.g., a liquid) present in the first compartment. The shape of the separating stopper is not particularly restricted. It has a suitable three-dimensional shape to ensure that, in a first position, the two compartments are sealed off from one another. The separating stopper may be of any suitable shape: for example, cylindrical shapes, cylindrical shapes with rounded sides, dumbbell-shaped, or cuboid.

In any case, when a force, particularly a manual force is exerted, the first plug should be movable at the first end of the body and hence towards a component (e.g., a liquid component) disposed in the first compartment.

The second plug is preferably an elastic and flexible material and is preferably made of rubber, such as natural or synthetic rubber, plastics, such as elastomers, thermoplastics, thermoplastic elastomers and the like. The material of the second plug should provide a seal between the first and second compartments, e.g., during storage, when the second plug is in a first position as described herein.

According to a preferred embodiment according to the present disclosure, the second plug is of a suitable shape, size and/or material that on the one hand will prevent it from being pushed out of its initially fixed and defined position in the cylindrical body but on the other hand will assist the intended displacement of the second plug into the bypass. Conveniently, this can be achieved by the suitable provision of a second plug having a suitable shape with (adhesive) bumps, lips, beads, ridges, or the like and/or by the choice of a suitable diameter, as described in U.S. Pat. No. 8,002,734.

According to the present disclosure, the term "form" is intended to refer to the outer shape or geometry. The term "size" is intended to refer to the dimensions, i.e., the ratios of magnitude.

In any embodiment, the second plug may have a larger outer diameter than the internal diameter of the body, so that sufficient pressure is built up between the inner wall of the body and the second plug to close the interface, although the latter is movable within in the body under the effect of force. The second plug is therefore mounted to be movable or displaceable and fluid tight within the body of the container.

In the body there is also a bypass in the form of a bulge that creates a detour line along the body. The bulge may occupy just a portion of the circumference of the body, or it may extend around the entire circumference of the body. Generally, the bulge is thinner than the diameter of the second plug. The bypass is not particularly restricted provided that its length is shorter than the height of the second plug, so that when the second plug is pushed into the bypass it opens up a plurality of passages for the contents of the first compartment (e.g., a first component such as a liquid reconstitution medium) to enter the second compartment and mix with a second component (e.g., a lyophilizate) therein. In other words, the bypass is a region in the body defines a bypass zone that is shorter along the longitudinal axis than the length of the second plug along the longitudinal axis, the bypass being arranged and having a size such that, when the second plug is pushed into the bypass zone and is located therein, the first component disposed in the first compartment is able to flow around the stopper. The bypass provided around at least a portion of the second plug therefore has a length L along its longitudinal axis which is shorter than the height H of the second plug along its longitudinal axis. The bypass is therefore preferably shorter than the second plug, thus producing a flow of liquid through the second plug when the second plug is in the bypass position.

In any embodiment, the bypass may be provided on one or more sides, i.e., on one or more sides of the body of the container. In any embodiment, the bypass is provided on only one side of the inner wall of the body. In a filled state for storage the second plug is located above the bypass zone (i.e., proximate the first end) and for mixing it is pushed into the bypass zone. Preferably, therefore, (adhesive) bumps, beads, ridges, or lips are provided in the bypass zone for releasably securing the second plug there and ensuring unimpeded passage of the contents of the first compartment (e.g., a liquid reconstitution medium) into the second compartment (e.g., a solid material or gel that is soluble and/or dispersible in the reconstitution medium).

If the contents of the first compartment are put under pressure when the second plug is disposed in a first operational position in the body, the second plug initially adheres to the inner wall of the body by frictional forces. If the frictional adhesion of the second plug to the wall of the body is not sufficient for a particular application, to prevent accidental movement, additional frictional force may be provided by adding projections such as small beads, lips, ridges or bumps to the second plug and/or to the inner wall of the body. The pressure therefore does not increase in the second compartment. As a result, a differential pressure is produced between the two compartments. By applying additional pressure, the frictional forces are overcome and the second plug is pushed in the direction of the bypass. As a result of this movement. At least a portion of the second plug is moved into the bypass, facilitating movement of the first component (e.g., a liquid component) from the first compartment into the second compartment where the two components are mixed together.

The present disclosure also provides a method of preparing a container for mixing two components, the method comprising the following steps:

(1) providing a body with a bypass, a first plug, and a second plug according to any of the embodiments disclosed herein;

(2) inserting the second plug into the body to a position wherein each first opening of the plurality is disposed in the first portion of the body and is longitudinally aligned with the bypass;

(3) depositing a second component via the second aperture into the second compartment;

(4) optionally, evaporating and evacuating a solvent from the second compartment, if the second component is dissolved and/or suspended therein;

(5) sealing the second end of the body;
(6) depositing a first component into the first compartment via the first aperture; and
(7) inserting the first plug into the body proximate the first end.

The process will hereinafter be described in detail; any individual features described in relation to the process also apply accordingly to the double compartment container and vice versa.

The conduits are not particularly restricted as to their shape and size. They may be selected at will depending the volume and/or viscosity of first component to be moved from the first compartment to the second compartment. Possible embodiments of the conduits include round, oval, oblong, triangular or rectangular cross-sectional shapes and combinations thereof. The conduits may also be arranged at defined spacings and angles from one another.

In any embodiment, the first plug and second plug may be rotationally symmetrical with respect to the central axis.

The first opening that is provided in the second plug is automatically closed by pressing in and positioning the second stopper in the container with the first opening contacting the inner surface of the wall thereof, so that it is not possible for one of the components to pass accidentally through the second plug.

Then the sealed container is taken to a filling station, where in step (6) it is filled with the first component (e.g., a reconstituting medium) through the first aperture. After the first compartment has been filled with an amount (e.g., a predetermined volume) of the first component (e.g., a dissolving or dispersing medium for the second component), the container is fitted with a closure (i.e., the first plug of step (7)). Preferably a stopper may be used as the first plug. However, it is also possible to use any other closure known in the art, provided that it is displaceable under the effect of pressure. It is particularly advantageous if the first plug at the liquid end is a stopper which contains an elastic material or consists thereof, such as plastics, rubber or rubber-like elastic material, such as elastomers, thermoplastics, elastomeric thermoplastics, etc.

The first plug is designed so that it also closes off any opening(s) provided at the first end of the body, so as to seal the container completely. It is particularly expedient if the first plug is supplied and inserted by means of a washing and sterilizing device or an autoclave along sterile corridors. After the container has been sealed it is taken out of the sterile area through an airlock; finally it is labeled and packaged. It will be understood that in this process all the surfaces and equipment are designed for aseptic operation.

According to the present disclosure the second plug thus performs a number of different functions. Initially, when assembling and filling the container, it functions as a partitioning structure to form two isolated compartments in the body. Then, the second plug functions as a temporary closure inside the body, to isolate the second component from the first component during storage. During use, the second plug performs two additional functions: 1) when the second plug is urged into the bypass by pressure applied to the first end of the container, the primary conduits facilitate transfer of the first component from the first compartment to the second compartment; and 2) after the first component has been transferred to the second compartment, the first plug urges the second plug out of the bypass and continued pressure applied to the first plug at the first end of the container causes the second plug to expel the blended first and second components in the second compartment to be expelled from the container.

In any embodiment, the double compartment container of the present disclosure is a container configured for single or multiple uses.

The measurements of the double compartment container depend on the volume of the mixture or dispersion which is to be produced. For example, in human medical practice, volumes of 10 ml are rarely exceeded, which means that volumes of up to about 20 ml are usually sufficient. In exceptional cases and for veterinary use however it is possible to exceed these volumes.

The present disclosure also provides a method of mixing a first component (e.g., a solid lyophilizate) and a second component (e.g., a liquid reconstitution medium) in a double compartment container, the container comprising:
 a body having a longitudinal axis, a first end with a first aperture, a second end including a second aperture opposite the first end, and a bypass disposed between the first and second ends;
  wherein the bypass has a length L;
 a first plug slidably disposed in the body proximate the first end;
 a second plug slidably disposed in the body between the first plug and the second end;
  wherein the first and second plugs define a first compartment disposed in the body between them;
  wherein a second compartment is disposed in the body between the second plug and the second end;
  wherein the second plug includes:
   a top surface facing the first plug;
   a bottom surface facing the second end;
   a side wall extending between the top surface and the bottom surface, the side wall comprising a circumferential first seal having a first edge proximate the top surface and a circumferential second seal having a second edge proximate the bottom surface;
   a primary conduit extending into the second plug from a first opening in the side wall; and
   a plurality of secondary conduits, each secondary conduit extending from the primary conduit to separate second openings in the bottom surface;
   wherein the first opening is disposed between the circumferential first seal and the circumferential second seal;
   wherein at least one of the secondary conduits directs liquid flow out of its second opening along a line that is not parallel to the longitudinal axis;
   wherein a distance D extends longitudinally from the first edge to the second edge;
   wherein a distance E extends longitudinally from the first edge to the first opening;
  wherein D≥L and E<L.

In order to mix the two components, the first plug is pushed towards the second plug by the application of external force, particularly force exerted manually, and at the same time pressure is applied to the first plug, causing the second plug to be pushed into the bypass, so that the first component has a passage to the compartment containing the second component. The two components may thus be mixed together without affecting the sterile conditions of the double compartment container.

Preferably the first plug is a stopper, particularly a rubber stopper. The two components are particularly preferably mixed together by holding the container vertically, i.e., with the second end oriented below the first end. In any embodiment, while the two components are mixed, the second end is fluidically sealed e.g., using a sealing disc with a flanged cap, but it is also possible to use any other suitable, optionally removable, closure.

The pressure on the first plug may be applied using the fingers, a stem or plunger attached to or in contact with the first plug, a suitable punch, or other suitable mechanical actuator, impulse, or means. Both the first component and the second plug then move toward the second end. The second plug moves into the bypass position and thereby opens a fluidic pathway between the first compartment and the second compartment via the plurality of primary conduits. The pressure exerted on the first component by the first plug allows the first component to flow through the fluidic pathway opened up by the bypass between the first and second compartments and to enter the second compartment containing the second component (e.g., a lyophilizate).

The first component (e.g., a reconstitution medium) combines with the second component (e.g., a solid lyophilizate) and the latter is dissolved and or suspended in the former. The first plug at the first end can be pressed right through to the second plug. The solution or suspension is finally completely reconstituted and is ready for use.

In any embodiment, combined (e.g., reconstituted) mixture of the first and second components can be distributed out of the container through the second aperture described herein. In these embodiments, the fluid-tight seal, if present on the container is converted from a closed state to an open state (e.g., by removing a cap, opening a valve, and/or piercing a pierceable seal).

The present disclosure also relates to the use of the container according to the invention in human and veterinary medicine.

The container and methods of the present disclosure have a number of advantages:

According to the present disclosure, in one embodiment, a double compartment container with a lyophilizate and a reconstitution solution is provided. Using the container according to the disclosure it is possible to dry a substance which is unstable in solution directly in the lyophilizer and then provide a double compartment system in the single body. Thus the construction according to the present disclosure allows problem-free storage of the two-component system without premature mixing and hence a loss of efficacy of the components taking place. The two-component system provided according to the present disclosure may be stored in the sterilized, pre-filled state ready for use. The mixing of the two components takes place after storage immediately before use. The double compartment container can be thrown away after use.

Using the double compartment container according to the invention a desired solution or suspension may be prepared immediately before use, resulting not only in a fast and reliable system, but also ease of manufacture and filling. This is an all-in-one solution, i.e., a container is obtained having two compartments which are separated from one another by a plug.

Using the double compartment container according to the invention it is possible to carry out reconstitution of a lyophilizate in a sealed two-compartment system, by simple maneuvers, without having to opening it and, thereby, possibly expose it to undesirable external microbial, chemical or physical influences.

The double compartment system described allows the container already in the lyophilizer to be tightly sealed. This gives rise to the advantages that contamination of the lyophilizate, particularly by particles, pathogens, and any foreign bodies, are avoided. Moreover, the lyophilizate is protected from moisture and oxygen. The container can be used as primary pack aging and stored in its clearly labeled form. The use of two component systems, particularly lyophilized preparations, can thus be made simpler. The container is not limited in any way and may be used for example in so called pen systems which are already on the market.

Turning to the drawings, FIG. 1 is a schematic side view, partially in section, of one embodiment of a body 100 of a container according to the present disclosure. The body 100 has a first end 102 and a second end 104 opposite the first end. The first end 102 has a first aperture 103 that provides access to (or egress from) the interior of the body 100. The second end 104 has a second aperture 107 (see FIG. 2) that also provides access to (or egress from) the interior of the body 100. Optionally, the second aperture 107 may be smaller than the first aperture 103, as shown in FIG. 1.

In any embodiment, the second end further comprises a coupling structure 106. The coupling structure 106 can be used to couple (e.g., fluidically couple) the body 100 to an infusion device, thereby permitting transfer of a composition contained in the body to the infusion device. Non-limiting examples of suitable coupling structures include Luer fittings (e.g., Luer-slip and Luer-lock type fittings) that are well known in the art. Nonlimiting examples of infusion devices include a catheter, a cannula, a needle, or a microneedle device.

In any embodiment, the coupling structure 106 may comprise a valve (not shown). The valve may have an open position that permits fluid flow into or out of the container and a closed position that does not permit flow into our out of the container.

The body 100 of the container further comprises a bypass 110. The bypass 110 divides the body 100 into three portions: a first portion 100*a* proximate the first end 102, a second portion 100*b* proximate the second end 104, and a bypass portion 100*c* disposed between the first portion and the second portion of the body. The cross-sectional diameter of the interior of the body 100 is larger in the bypass portion 100*c* than in the first portion 100*a* and second portion 100*b*.

FIG. 2 shows a top view of the body 100 of FIG. 1. The body 100 comprises wall 101 that defines a cylindrical inner volume that is bounded by a first aperture 103 at one end and a smaller second aperture 107 at the other end. Although the inner volume of the illustrated embodiment is cylindrical, a person having ordinary skill in the art will recognize that other shapes are possible. Also shown in FIG. 2 is the bypass 110 in which the cross-sectional area of the interior volume of the body 100 is larger than in other portions of the body The body 100 can be fabricated from any suitable material for containing two components that are intended to be mixed together. Preferably, the material is substantially inert with respect to interaction with either of the components to be mixed. In any embodiment, the body 100 is molded glass or plastic (e.g., thermoplastic) material, both of which can provide visual observation of the mixing process as it proceeds in the container. Alternatively, the body 100 may be fabricated from a metal (e.g., stainless steel) using processes that are well known in the art.

Figure 3:
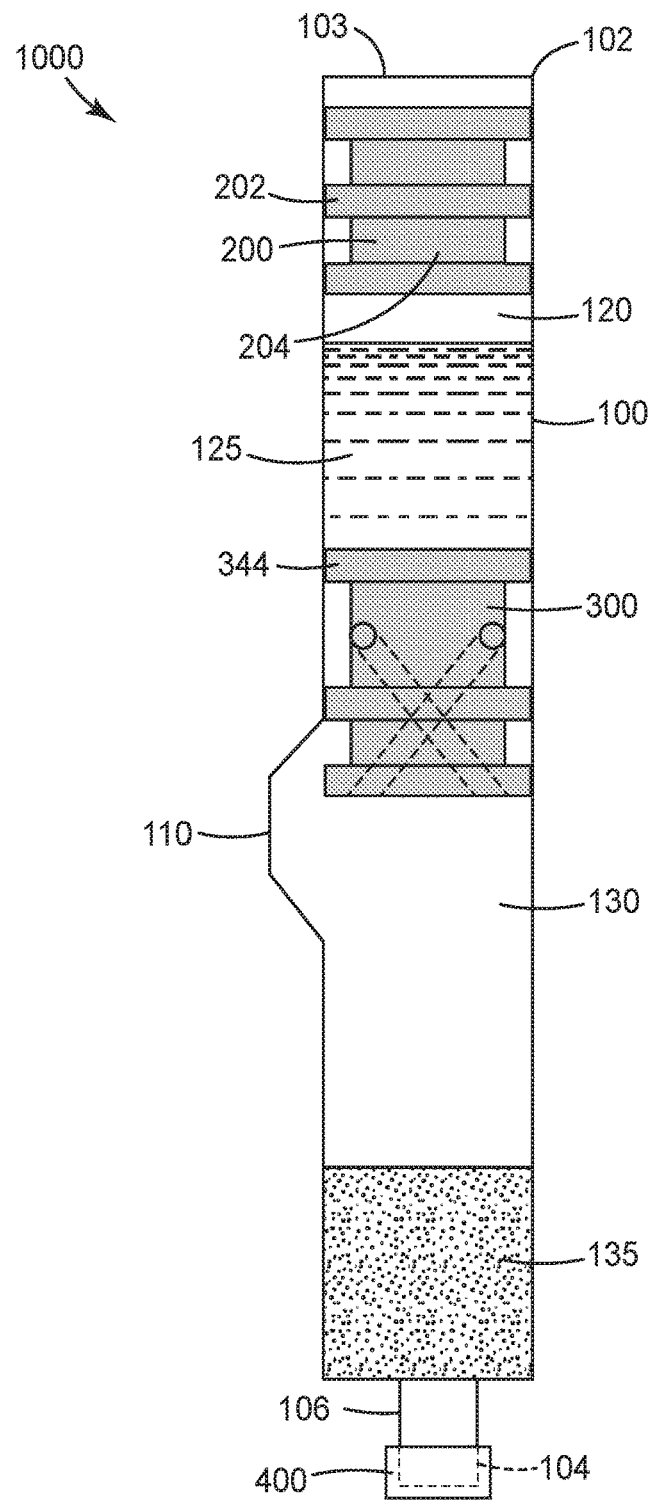
FIG. 3 is a schematic side view, partially in section, of one embodiment of a container according to the present disclosure.

FIG. 3 shows a schematic side view, partially in section, of one embodiment of a container 1000 according to the present disclosure. The container 1000 comprises a body 100 having a first end 102 with a first aperture 103, a second end 104, and a bypass 110 as described herein; the body 100 having a first plug 200 and a second plug 300 disposed therein. At least a portion of a circumferential first seal (first seal 344, described below) of the second plug 300 is disposed in the first portion (first portion 100a of FIG. 1) of the body 100. In this position, the second plug 300 divides the interior volume of the body 100 into two fluidically-isolated portions—a first compartment 120 proximate the first end 102 of the body and a second compartment 130 proximate the second end 104 of the body. Although not a requirement of every embodiment of the container of the present disclosure, in the illustrated embodiment of FIG. 3, the first compartment contains a liquid first component 125 and the second compartment contains a solid second component 135.

The container 1000 further comprises an optional openable seal 400 that fluidically seals the second end 104 of the body 100. In any embodiment, the seal 400 may be a fluid-tight seal wherein, in a closed configuration, the fluid-tight seal prevents fluid flow into or out of the second aperture. In any embodiment, the openable seal 400 may comprise a durable seal such as a plastic cap, for example, attached by friction fit to the second end 104 of the body 100. Alternatively or additionally, the openable seal 400 may comprise a frangible seal such as a plastic or metal foil film, for example, that is adhesively secured to the second end 104 of the body 100.

At least partially disposed in the body 100 proximate the first end 102 is a first plug 200. The first plug 200 may take the form of any shape that can form a moveable, fluid-tight seal in the body 100 of the container 1000. Optionally, the first plug 200 may comprise one or more extension 202 extending from a central section 204. The extensions 202 can reduce the amount of friction between the first plug 200 and the body 100, thereby facilitating movement (i.e., reducing the amount of force necessary for movement) of the first plug 200 through the body. In the illustrated embodiment of FIG. 3, the extensions 202 provide seals that hold the liquid first component 125 in the first compartment 120 during a storage period until the first and second components are mixed in the container 1000 as described herein.

The first plug 200 is preferably an elastic and flexible material and is preferably made of rubber, such as natural or synthetic rubber, plastics, such as elastomers, thermoplastics, thermoplastic elastomers and the like using processes (e.g., injection molding processes) that are well known in the art.

Figure 4A:
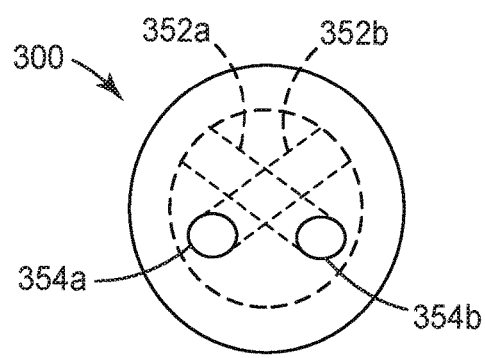
FIG. 4A is a bottom view of the second plug of FIG. 3.
Figure 4B:
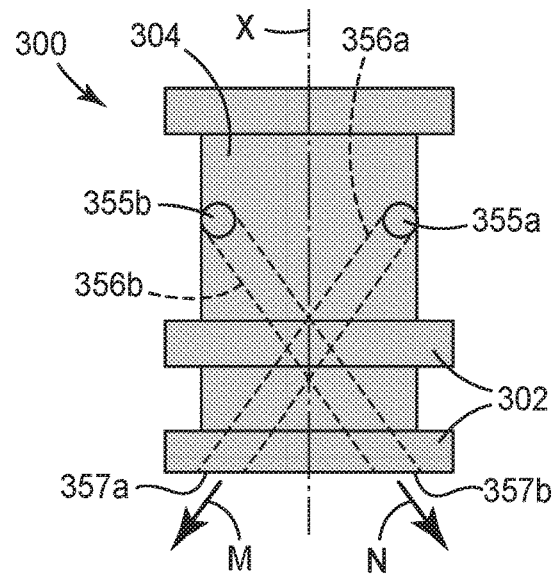
FIGS. 4B and 4C are side view of the second plug of FIG. 3.
Figure 4C:
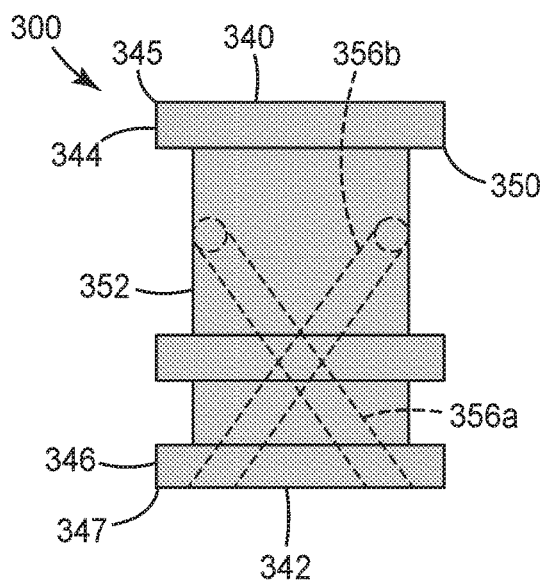

FIGS. 4A-4C show various views of one embodiment of the second plug 300 of FIG. 3. The second plug 300 is shaped and dimensioned to sealingly fit inside the body of a container of the present disclosure. The second plug 300 has a central section 304 with optional extensions 302 extending therefrom. The extensions 302 can reduce the amount of friction between the second plug 300 and the body 100, thereby facilitating movement (i.e., reducing the amount of force necessary for movement) of the second plug 200 through the body 100. In addition, the second plug 300 has an axial top surface 340 that faces the first end of the body, an axial bottom surface 342 that faces the second end of the body, and a primary conduit 352 extending into the second plug.

The primary conduit extends from a radial first opening (first opening 350) into the central section 304 of the second plug 300. In addition, a plurality of secondary conduits (secondary conduits 356a and 356b, respectively) extend from second openings (second openings 355a and 355b, respectively) located in the primary conduit 352 to separate third openings (third openings 357a and 357b, respectively) at the bottom surface 342 of the second plug 300. It is contemplated that the second plug may comprise two or more primary conduits (not shown). The second plug may have 2, 3, 4, 5, 6, 8, 10, 12, 15, or 20 primary conduits extending there from the primary conduit. Thus, in any embodiment, the second plug may include 2-4 primary conduits, 2-6 primary conduits, 2-8 primary conduits, 2-10 primary conduits, 2-12 primary conduits, 4-10 primary conduits, or 10-20 primary conduits.

At least one of the secondary conduits directs liquid flow out of the second opening along a line that is not parallel to the longitudinal axis "X" of the second plug 300. As shown by lines "M" and "N" in FIG. 4B, both secondary conduits (secondary conduits 356a and 356b) direct liquid flow out of their respective second openings along a line that is not parallel to the longitudinal axis "X" of the second plug 300. In any embodiment, at least one of the secondary conduits (e.g., secondary conduit 356b) directs liquid flow out of the second opening (e.g., second opening 357b) along a line that forms a compound angle with respect to the longitudinal axis X of the second plug 300, as shown in FIGS. 4A-4C. In any embodiment, two or more of the secondary conduits each directs liquid flow out of its second opening along a line that forms a compound angle with respect to the longitudinal axis.

The configuration of the secondary conduits wherein at least one directs liquid flow alone a line that is not parallel to the longitudinal axis creates additional turbulence (e.g., by deflection of the liquid flow off the side wall of the body) such that the component disposed in the second compartment can be mixed more rapidly and thoroughly that when the liquid flow is directed along a line that is parallel to the longitudinal axis.

In any embodiment (not shown), at least one of the plurality of secondary conduits directs liquid flow out of the second opening along a line that is not parallel to the longitudinal axis and at least one of the plurality of secondary conduits directs liquid flow out of the second opening along a line that is substantially parallel to the longitudinal axis. "Substantially parallel", as used herein refers to a line that intersects the longitudinal axis to form an angle that is less 3°.

The second plug 300 is preferably an elastic and flexible material and is preferably made of rubber, such as natural or synthetic rubber, plastics, such as elastomers, thermoplastics, thermoplastic elastomers and the like using processes (e.g., injecting molding processes) that are well known in the art. The primary conduits may be formed while the second plug is formed or, alternatively, may be formed (e.g., using a laser drilling process) after the second plug is formed.

Figure 5:
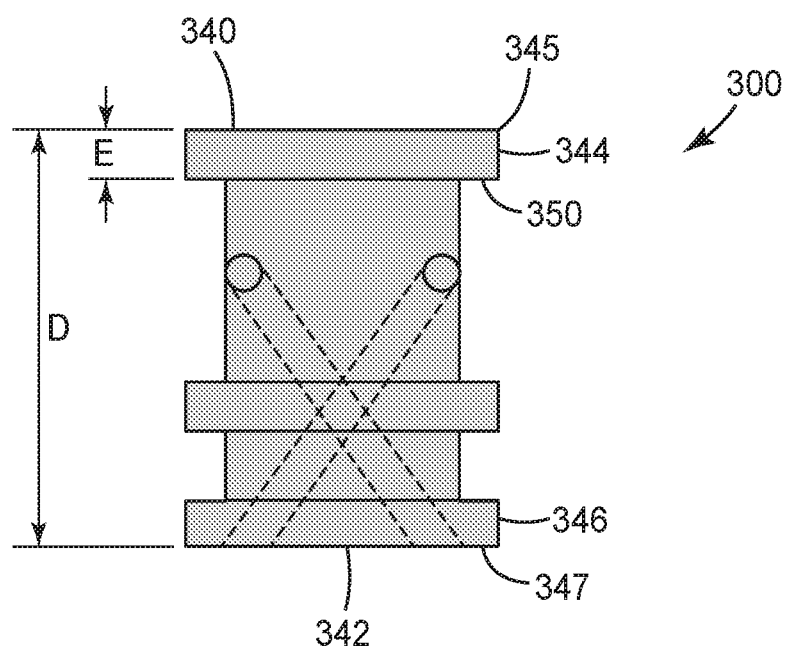
FIG. 5 is a side view of the second plug of FIG. 3, showing certain dimensional features and showing the relationship of the primary conduits to the longitudinal axis of the second plug.

The second plug 300 (see FIG. 5) comprises at least two portions (circumferential seals 344 and 346, respectively) that, when disposed in the first or second portion of the body of the container of the present disclosure, form a fluid-tight seal in the container. The circumferential first seal 344 comprises a first edge 345 proximate the top surface 340 of the second plug 300. The circumferential second seal 346 comprises a second edge 347 proximate the bottom surface 342 of the second plug 300. The first opening (first openings 350) is disposed between the circumferential first seal 344 and the circumferential second seal 346. A distance "E" extends from the first edge 345 to the first opening (i.e., first opening 350 of the primary conduit 352 of FIG. 5) that lies closest to the first edge. Distance E is less than distance L. A distance "D" extends longitudinally from the first edge 345 to the second edge 347.

Figure 6:
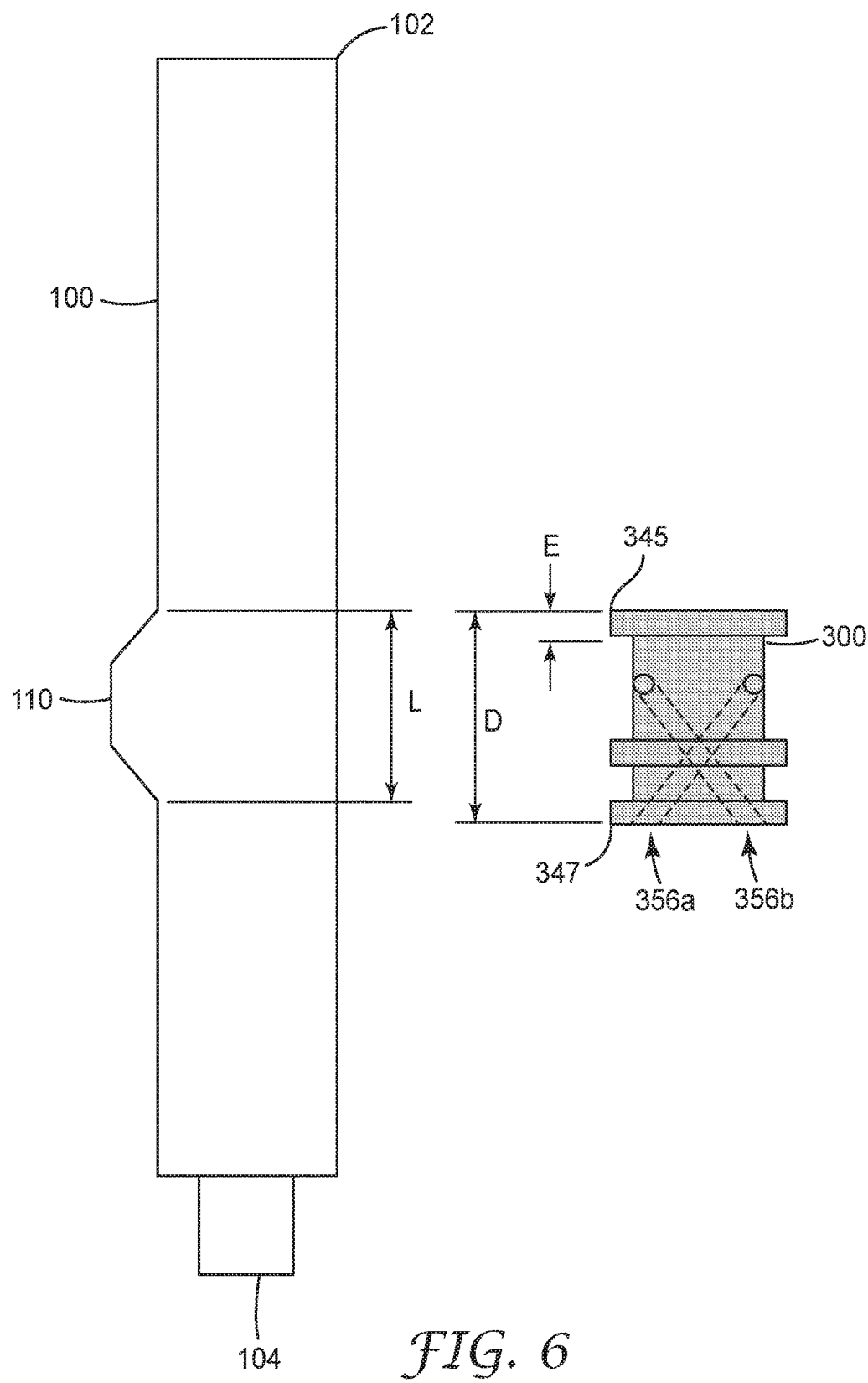
FIG. 6 is a side view of the body and the second plug of FIG. 3 showing certain dimensional relationships of the features of the bypass and the second plug.

FIG. 6 shows side views of the body 100 and second plug 300 of the container 1000 of FIG. 3. In the illustrated embodiment, the axial length D between the first edge 345 and second edge 347 of the second plug 300 is greater than the axial length L of the bypass 110 of the body 100. This relationship ensures that, as the second plug 300 moves through the bypass region (see bypass region 100c of FIG. 1), either the first edge 345 and/or the second edge 347 is in circumferential contact with the body 100. This further ensures that any fluid flow from the first end 102 side of the second plug 300 to the second end 104 side of the second plug must be through the primary conduit 252 and one or more of the plurality of secondary conduits (i.e., secondary conduits 356a and 356b, respectively).

In use, a container according to the present disclosure can be used to mix two components (e.g., a fluid component (e.g., a liquid) and a solid component) that have been kept isolated from each other in the container for a period of time. FIGS. 7-9 show schematic side views, partially in section of a container 1000 in various stages of a process of mixing two components according to the method.

FIG. 7 shows a container 1000 comprising a body 100 with a first end 102, a second end 104, and a bypass 110, each as described herein. Disposed in the first portion (first portion 100a of FIG. 1) of the body 100 proximate the first end 102 is a first plug 200, as described herein. Located in a first operational position in the first portion (first portion 100a of FIG. 1) of the body 100 is a second plug 300 as described herein. The second plug 300 comprises a primary conduit 352 and a plurality of secondary conduits (secondary conduits 356a and 356b) extending through the second plug 300 from the primary conduit 352 to the second surface of the second plug as disclosed herein. Positioned between the first plug 200 and the second plug 300 is a first compartment 120 containing a first component 125 (e.g., a liquid in which a second component can be dissolved and/or suspended). In any embodiment, the first component 125 can be an aqueous liquid selected form the group consisting of water, buffered water, an aqueous saline solution, and combinations thereof.

In any embodiment, the first component 125 may be present in the first compartment in a predetermined quantity. Positioned between the second plug 300 and the second end 104 is a second compartment 130 containing a second component 135 (e.g., a lyophilized solid capable of dissolving or suspending in the first component 125). In any embodiment, the second component 135 may be present in the form of a powder. In any embodiment, the second component may comprise a predetermined quantity of a pharmaceutically-active compound. In any embodiment the powder may comprise a vaccine. In any embodiment the powder may comprise a small molecule, a protein, a peptide a glycoprotein, a hormone, or a polynucleotide. The powder may be a naturally derived compound or a synthetic compound. The container 1000 further comprises a seal 400 that is impervious to the first and second components (125 and 135, respectively) disposed in the container. Thus, the container 1000 shown in FIG. 7 has a first component 125 and second component 135 contained therein in a configuration that can be used to store the components prior to the mixing process described herein.

According to the method, the first plug 200 is urged under pressure (e.g., manual or machine pressure) into the body 100 toward the second end 104, as shown in FIG. 8. In order to facilitate movement of the first plug 200 into the body, a pushing object (e.g., a stem, not shown, optionally attached to the first plug) can be used to apply force to the first plug in the direction of arrow "A". Force against the first plug 200 is translated through the first compartment 120 and first component 125 to the second plug 300, causing the second plug to move toward the second end 104 and into a second operational position, as shown in FIG. 8. As the top surface 340 (shown in FIG. 7) of the second plug 300 moves into the bypass 110, the force against the first plug 200 caused the first component 125 to move into the bypass 110 (as shown by arrow "B"), through the primary conduit 352, through the secondary conduits 356a and 356b, and out the second plug 300 into the second compartment 130, as shown by arrows "C" in FIG. 8. Upon entering the second compartment 130, flow of the first component 125 causes turbulence (not shown), which facilitates rapid dissolution and/or suspension of the second component 135 causing formation of the mixture 170 as substantially all of the first component 125 is transferred under pressure from the first compartment 120 to the second compartment 130. Advantageously, in any embodiment, the method does not require addition shaking (e.g., manual and/or mechanically-assisted shaking) in order to achieve a uniform mixture (or suspension) of the first and second components after the first component has been transferred into the second compartment.

In use, a container according to the present disclosure can be used in a method to mix two components (e.g., a fluid component (e.g., a liquid and a solid component) and further to distribute the combination of the two components. FIGS. 7-10 show schematic side views, partially in section of a container 1000 in various stages of a process of mixing two components according to the method.

It is contemplated that management of air pressure within multi-compartmental containers is a factor during storage and/or subsequent use of the container to mix the components disposed in the compartments. Avoiding the build-up of air pressure within the second compartment will prevent excessive back pressure from developing as the first and second plugs are urged toward the second end of the container. Possible solutions include, but are not limited to, evacuating air from the second compartment (e.g., during lyophilization of the second component) or inserting a vent (e.g., a needle) through the second aperture or actuating a valve or vent (not shown) at the second aperture while the first component is transferred form the first compartment to the second compartment.

This method includes the steps shown in FIGS. 7-9 and described above. After the first and second components have been combined to form the mixture 170, the seal 400 is removed from the second end of the container, thereby exposing the second aperture (see FIG. 2; not shown in FIGS. 7-10). Continued force against the first plug 200 in the direction of arrow A is translated to the second plug and the mixture 170, causing the mixture 170 to flow out the second end 104, as shown by arrow "P" in FIG. 10.

In any embodiment of the container of the present disclosure, the bottom surface of the second plug may take a form other than a plane that is orthogonal to the longitudinal axis of the second plug. Thus, in any embodiment, the bottom surface of the second plug may take the form of a non-planar shape. Non-limiting examples of suitable shapes of the bottom surface include a segment of a sphere, a hemisphere, a catenoid, a paraboloid of revolution, a truncated cylinder, a cone, a truncated cone, and a frustum. Advantageously, the shaped surface can perform at least two functions: 1) a projecting bottom surface of the second plug may better conform to the shape of the second aperture at the second end and, thus, facilitate expulsion of the entire mixture from the container, and 2) a shaped bottom surface of the second plug can create additional turbulence in the second compartment, thereby facilitating more-rapid dissolution and/or dispersion of the second component into the first component.

Figure 11:
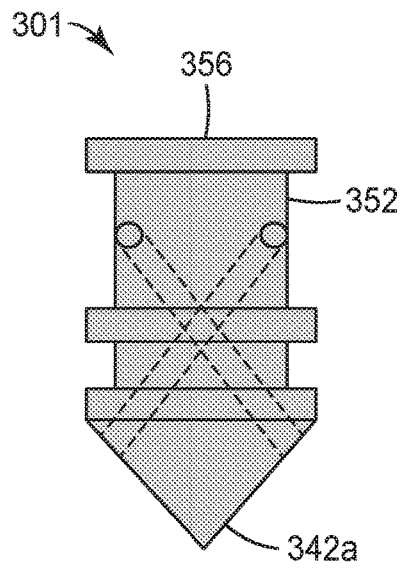
FIG. 11 is a schematic side view of one embodiment of a second plug having a shaped bottom surface according to the present disclosure.
Figure 12:
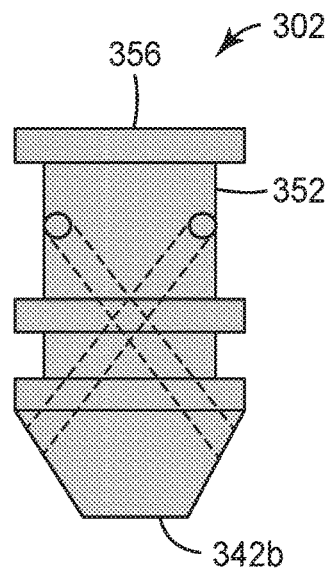
FIG. 12 is a schematic side view of an alternative embodiment of a second plug having a shaped bottom surface according to the present disclosure.
Figure 13:
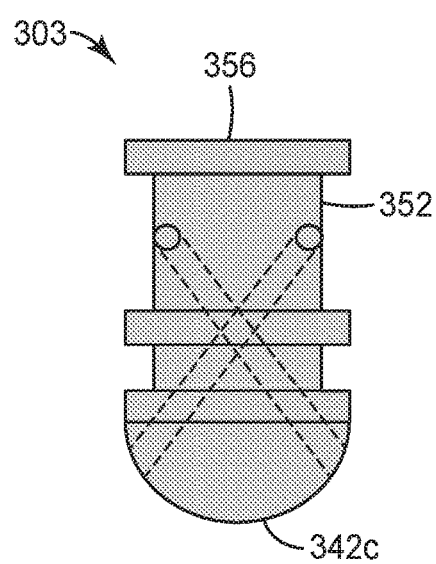
FIG. 13 is a schematic side view of an alternative embodiment of a second plug having a shaped bottom surface according to the present disclosure.

FIGS. 11-13 show three embodiments of second plugs (301, 302, and 303, respectively) having shaped bottom surfaces (342a, 243b, and 342c, respectively), each second plug having a primary conduit 352 extending into the plug and a plurality of secondary conduits 356 extending from the primary conduit to the bottom surface (i.e., bottom surfaces 342a, 342b, and 342c, respectively) of the second plug. In each of the illustrated embodiments, at least one of the primary conduits 352 directs liquid flow out of the second opening along a line that is not parallel to the longitudinal axis (not shown). The second plug 301 of FIG. 11 comprises a conical-shaped bottom surface 342a. The second plug 302 of FIG. 12 comprises a frustoconical-shaped bottom surface 342b. The second plug 303 of FIG. 13 comprises a hemispherical-shaped bottom surface 342c.

Although the primary conduits (e.g., primary conduits 352 of FIGS. 11-13) of the illustrated embodiments discussed above are shown as creases, notches, or indentations, it is also contemplated that a primary conduit of the present disclosure can take the form of a through-hole or a dead-end channel.

Figure 14A:
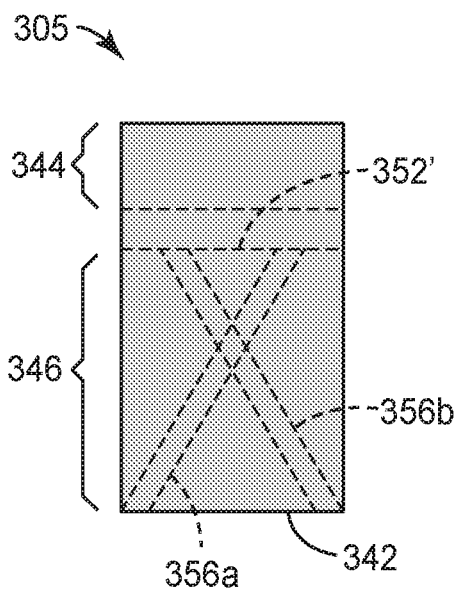
FIGS. 14A and 14B are schematic side views of two alternative embodiments of second plugs according to the present disclosure.

FIG. 14A shows one embodiment of a second plug 305 having a primary conduit 352' that defines a through-hole extending laterally through the plug 305. The primary conduit 352' is oriented substantially perpendicular to the longitudinal axis of the second plug 305. Extending from the primary conduit 352' to the second surface 342 of the second plug 305 are a plurality of secondary conduits (secondary conduits 356a and 356b. In these embodiments, when the primary conduit 352' is placed into fluid communication with the first compartment of the container according to the present disclosure (i.e., when the feeder conduit 356 and the circumferential first seal 344 are both disposed in the bypass, not shown), the first component (e.g., a liquid) can move through the second plug 305 via the primary conduit 352' and the secondary conduits 356a and 356b. Also shown in FIG. 14A is the circumferential second seal 346.

Figure 14B:
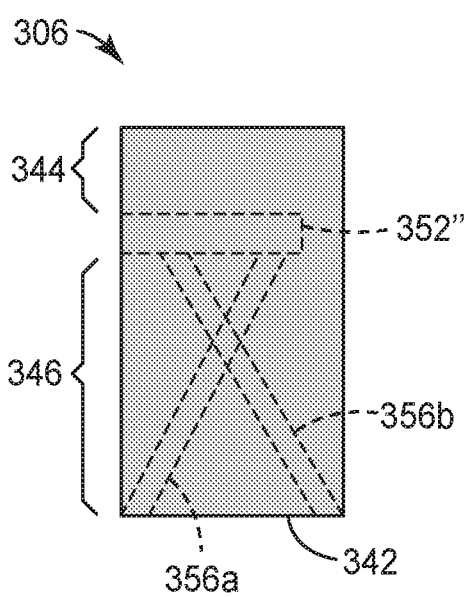

In the illustrated embodiment of FIG. 14B, the primary conduit 352" is a dead-end channel that extends into the second plug 305. Extending from the primary conduit 352" to the second surface 342 of the second plug 305 are a plurality of secondary conduits (secondary conduits 356a and 356b. In these embodiments, when the primary conduit 352" is placed into fluid communication with the first compartment of the container according to the present disclosure (i.e., when the feeder conduit 356' and the circumferential first seal 344 are both disposed in the bypass, not shown), the first component (e.g., a liquid) can move through the second plug 305 via the primary conduit 352" and the secondary conduits 356a and 356b. Also shown in FIG. 14B is the circumferential second seal 346.

It is contemplated that the second plug (not shown) may comprise a plurality of primary conduits similar to primary conduits 352' or 352" from which at least one secondary conduit extends to the second surface of the plug.

Exemplary Embodiments

Embodiment A is a container, comprising:
a body having a longitudinal axis, a first end with a first aperture, a second end including a second aperture opposite the first end, and a bypass disposed between the first and second ends;
wherein the bypass has a length L;
a first plug slidably disposed in the body proximate the first end;
a second plug slidably disposed in the body between the first plug and the second end;
wherein the first and second plugs define a first compartment disposed in the body between them;
wherein a second compartment is disposed in the body between the second plug and the second end;
wherein the second plug includes:
a top surface facing the first plug;
a bottom surface facing the second end;
a side wall extending between the top surface and the bottom surface, the side wall comprising a first circumferential seal having a first edge proximate the top surface and a second circumferential seal having a second edge proximate the bottom surface;
a primary conduit extending into the second plug from a first opening in the side wall; and
a plurality of secondary conduits, each secondary conduit extending from the primary conduit to separate second openings in the bottom surface;
wherein the first opening is disposed between the circumferential first seal and the circumferential second seal;
wherein at least one of the secondary conduits directs liquid flow out of its second opening along a line that is not parallel to the longitudinal axis;
wherein a distance D extends longitudinally from the first edge to the second edge;
wherein a distance E extends longitudinally from the first edge to the first opening;
wherein D≥L and E<L.

Embodiment B is the container of Embodiment A, wherein two or more of the primary conduits each directs liquid flow out of its second opening along a line that is not parallel to the longitudinal axis.

Embodiment C is the container of Embodiment A or Embodiment B, wherein the bottom surface substantially defines a shape selected from the group consisting of a segment of a sphere, a hemisphere, a catenoid, a paraboloid of revolution, a truncated cylinder, a cone, a truncated cone, and a frustum.

Embodiment D is the container of any one of the preceding Embodiments, wherein at least one of the secondary conduits directs liquid flow out of its second opening along a line that forms a compound angle with respect to the longitudinal axis.

Embodiment E is the container of Embodiment D; wherein two or more of the secondary conduits each directs liquid flow out of its second opening along a line that forms a compound angle with respect to the longitudinal axis.

Embodiment F is the container of any one of the preceding claims, wherein the second compartment has a lyophilized reagent disposed therein.

Embodiment G is the container of Embodiment F, wherein the lyophilized reagent comprises a predetermined amount of a pharmaceutically-active compound.

Embodiment H is the container of any one of the preceding Embodiments, further comprising a stem operatively coupled to the first plug.

Embodiment I is the container of any one of the preceding Embodiments, wherein the second end comprises a coupling structure.

Embodiment J is the container of any one of the preceding Embodiments, wherein the container includes an openable fluid-tight seal proximate the second aperture wherein, in a closed configuration, the fluid-tight seal prevents fluid flow into or out of the second aperture.

Embodiment K is the container of Embodiment I or Embodiment J, wherein the coupling structure is adapted to couple to a needle or a microneedle device to the container.

Embodiment L is the container of Embodiment K, wherein the coupling structure comprises a valve having an open position that permits fluid flow out of the container and a closed position that does not permit fluid flow out of the container.

Embodiment M is the container of any one of the preceding Embodiments; wherein the first compartment contains a predetermined quantity of a first component to be mixed with a second component; wherein, at ambient temperature, the first component comprises a gas, a liquid, or a gel.

Embodiment N is the container of Embodiment M, wherein the second compartment contains a predetermined quantity of a second component to be mixed with the first component; wherein, at ambient temperature, the second component comprises a gas, a liquid, a gel, a substantially dry solid, or a paste.

Embodiment O is a method of mixing first and second components of a composition, the method comprising:
bringing the first component, which is disposed in the first compartment of a container of Embodiment N, into contact with the second component, which is disposed in the second compartment of the vessel;
wherein the first component comprises a fluid;
wherein the second component comprises a fluid or a solid;
wherein bringing the first component into contact with the second component comprises urging the first plug toward the second end until at least one first opening is in fluid communication with the bypass, the first compartment, and the second compartment;
wherein urging the first plug toward the second end comprises urging at least a portion of the first component from the first compartment into the second compartment.

Embodiment P is a method of mixing first and second components of a composition and distributing the composition, the method comprising:
bringing the first component, which is disposed in the first compartment of a container of Embodiment N, into contact with a second component, which is disposed in the second compartment of the vessel;
wherein the first component is selected from the group consisting of a gas, a liquid, and a gel;
wherein the second component is selected from the group consisting of a gas, a liquid, a gel, a powder, and a paste;
wherein bringing the first component into contact with the second component comprises urging the first plug toward the second end until at least one first opening is in fluid communication with the bypass, the first compartment, and the second compartment;
wherein urging the first plug toward the second end comprises transferring a predetermined volume of the first component from the first compartment into the second compartment to form the composition; and
converting the second end from a closed state to an open state;
wherein, after the predetermined volume of the first component is transferred into the second compartment, urging the first plug toward the second end further comprises urging the second plug toward the second end;
wherein urging the second plug toward the second end comprises distributing at least a portion of the composition out of the body via the second aperture.

Embodiment Q is the method of Embodiment P, wherein converting the second end of the container from a closed state to an open state comprises converting a fluid-tight seal from a closed state to an open state.

Embodiment R is the method of Embodiment P or Embodiment Q, wherein converting the second end from a closed state to an open state comprises breaching a seal.

Embodiment S is the method of any one of Embodiments P through R, wherein converting the second end from a closed state to an open state comprises adjusting a valve from a closed state to an open state.

Embodiment T is the method of any one of Embodiments P through S, further comprising fluidically coupling the second aperture to an infusion device.

Embodiment U is the method of Embodiment T, wherein the infusion device is selected from a group consisting of a catheter, a cannula, a needle, or a microneedle device.

Embodiment V is the method of any one of Embodiment P through U, wherein the first component comprises a liquid, wherein the second component comprises a substantially dry solid.

Embodiment W is the method of Embodiment V, wherein the substantially dry solid comprises a powder.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A container, comprising:
a body having a longitudinal axis, a first end with a first aperture, a second end including a second aperture opposite the first end, and a bypass disposed between the first and second ends;

wherein the bypass has a length L;
a first plug slidably disposed in the body proximate the first end;
a second plug slidably disposed in the body between the first plug and the second end;
wherein the first and second plugs define a first compartment disposed in the body between them;
wherein a second compartment is disposed in the body between the second plug and the second end;
wherein the second plug includes:
a top surface facing the first plug;
a bottom surface facing the second end;
a side wall extending between the top surface and the bottom surface, the side wall comprising a first circumferential seal having a first edge proximate the top surface and a second circumferential seal having a second edge proximate the bottom surface;
a primary conduit extending into the second plug from a first opening in the side wall; and
a plurality of secondary conduits, each secondary conduit extending from the primary conduit to separate second openings in the bottom surface;
wherein the first opening is disposed between the circumferential first seal and the circumferential second seal;
wherein at least one of the secondary conduits directs liquid flow out of its second opening along a line that is not parallel to the longitudinal axis;
wherein a distance D extends longitudinally from the first edge to the second edge;
wherein a distance E extends longitudinally from the first edge to the first opening;
wherein D≥L and E<L.

2. The container of claim 1, wherein two or more of the secondary conduits directs liquid flow out of the second opening along a line that is not parallel to the longitudinal axis.

3. The container of claim 1, wherein the bottom surface substantially defines a shape selected from the group consisting of a segment of a sphere, a hemisphere, a catenoid, a paraboloid of revolution, a truncated cylinder, a cone, a truncated cone, and a frustum.

4. The container of claim 1, wherein at least one of the secondary conduits directs liquid flow out of its second opening along a line that forms a compound angle with respect to the longitudinal axis.

5. The container of claim 4; wherein two or more of the secondary conduits each directs liquid flow out of its second opening along a line that forms a compound angle with respect to the longitudinal axis.

6. The container of claim 1, wherein the second compartment has a lyophilized reagent disposed therein.

7. The container of claim 1, further comprising a stem operatively coupled to the first plug.

8. The container of claim 1, wherein the second aperture comprises a coupling structure.

9. The container of claim 8, wherein the coupling structure is adapted to couple to a needle or a microneedle device to the container.

10. The container of claim 1, wherein the container includes an openable fluid-tight seal proximate the second aperture wherein, in a closed configuration, the fluid-tight seal prevents fluid flow into or out of the second aperture.

11. The container of claim 1; wherein the first compartment contains a predetermined quantity of a first component to be mixed with a second component; wherein, at ambient temperature, the first component comprises a gas, a liquid, or a gel.

12. The container of claim 11, wherein the second compartment contains a predetermined quantity of a second component to be mixed with the first component; wherein, at ambient temperature, the second component comprises a gas, a liquid, a gel, a substantially dry solid, or a paste.

13. A method of mixing first and second components of a composition, the method comprising:
providing the container of claim 12;
bringing the first component, which is disposed in the first compartment of the container, into contact with the second component, which is disposed in the second compartment of the container;
wherein the first component comprises a fluid;
wherein the second component comprises a fluid or a solid;
wherein bringing the first component into contact with the second component comprises urging the first plug toward the second end until at least one first opening is in fluid communication with the bypass, the first compartment, and the second compartment;
wherein urging the first plug toward the second end comprises urging at least a portion of the first component from the first compartment into the second compartment.

14. A method of mixing first and second components of a composition and distributing the composition, the method comprising:
providing the container of claim 12;
bringing the first component, which is disposed in the first compartment of the container, into contact with the second component, which is disposed in the second compartment of the container;
wherein the first component is selected from the group consisting of a gas, a liquid, and a gel;
wherein the second component is selected from the group consisting of a gas, a liquid, a gel, a powder, and a paste;
wherein bringing the first component into contact with the second component comprises urging the first plug toward the second end until at least one first opening is in fluid communication with the bypass, the first compartment, and the second compartment;
wherein urging the first plug toward the second end comprises transferring a predetermined volume of the first component from the first compartment into the second compartment to form the composition; and
converting the second end from a closed state to an open state;
wherein, after the predetermined volume of the first component is transferred into the second compartment, urging the first plug toward the second end further comprises urging the second plug toward the second end;
wherein urging the second plug toward the second end comprises distributing at least a portion of the composition out of the body via the second aperture.

15. The method of claim 14, wherein converting the second end of the container from a closed state to an open state comprises converting a fluid-tight seal from a closed state to an open state.

16. The method of claim 14, wherein converting the second end from a closed state to an open state comprises breaching a seal.

17. The method of claim 14, wherein converting the second end from a closed state to an open state comprises adjusting a valve from a closed state to an open state.

18. The method of claim 14, further comprising fluidically coupling the second aperture to an infusion device.

19. The method of claim 18, wherein the infusion device is selected from a group consisting of a catheter, a cannula, a needle, or a microneedle device.

20. The method of claim 14, wherein the first component comprises a liquid, wherein the second component comprises a substantially dry solid.

\* \* \* \* \*